(12) United States Patent
Matsutani et al.

(10) Patent No.: US 6,214,030 B1
(45) Date of Patent: Apr. 10, 2001

(54) SUTURE NEEDLE

(75) Inventors: Kanji Matsutani; Takayuki Matsumoto, both of Takanezawa-machi (JP)

(73) Assignee: Mani, Inc., Tochigi (JP)

( * ) Notice: Subject to any disclaimer, the term of this patent is extended or adjusted under 35 U.S.C. 154(b) by 0 days.

(21) Appl. No.: 09/434,818

(22) Filed: Nov. 5, 1999

Related U.S. Application Data

(63) Continuation-in-part of application No. 09/131,802, filed on Aug. 10, 1998, now abandoned.

(51) Int. Cl.[7] .................................................. A61B 17/06
(52) U.S. Cl. ............................................................ 606/223
(58) Field of Search .................................. 606/224–228, 606/232, 223, 222, 144, 146, 148, 139

(56) References Cited

U.S. PATENT DOCUMENTS 3,160,157 * 12/1964 Chisman .......................... 606/223 X

* cited by examiner

Primary Examiner—Henry J. Recla
Assistant Examiner—Vikki Hoa Trinh
(74) Attorney, Agent, or Firm—Muramatsu & Associates

(57) ABSTRACT

A suture needle has a unique structure for reducing impalement resistance. The suture needle is formed with a base end portion formed at an end of the suture needle for engaging a suture thread, a tip portion formed at another end of the suture needle for impaling a tissue, and a tapered portion extending to the tip portion. The tapered portion has a cross-section without a cutting edge and a plurality of roughened regions formed in stripes extending in a substantially axial direction of the tapered portion. The roughened regions are provided solely on the tapered portion of the suture needle. The surface roughness of the roughened regions on the suture needle is about 2 $\mu$m–15 $\mu$m.

7 Claims, 5 Drawing Sheets

SUTURE NEEDLE

This application is a continuation-in-part of U.S. patent application Ser. No. 09/131,802, filed Aug. 10, 1998 entitled "Suture Needle" now abandoned.

FIELD OF THE INVENTION

The present invention relates to a suture needle for medical use, and more particularly, to a suture needle having reduced impalement resistance.

BACKGROUND OF THE INVENTION

Many kinds of medical suture needles have been used in accordance with their usage, for example, dull needles, square needles, and round needles have representatively been utilized.

A dull needle is used for suturing lever and the like, and a tip of the needle is dull. A square needle is generally used for suturing hard tissue such as skin and muscle, and has a sharp tip and a tapered portion with a shape of a polygonal pyramid, and each prescribed edge on the tapered portion is used as a cutting edge to cut and open a tissue.

A round needle is provided with a body with an appropriate cross-section and a conically tapered portion on the side of a tip thereof. Although the shape of the cross-sections of the conically tapered portion and the body are usually round, in place of the round cross-section, an oval which is sandwiched between two substantially parallel planes, a cross-section enclosed by four planes, and a cross-section which is sandwiched between two substantially parallel planes and of which central portion is constricted may be adopted. However, the tapered portion of a round needle is not adapted to be used as a cutting edge which is obtained by sharpening an edge like a square needle.

After piercing a tissue with a tip, a round needle enlarges the pierced hole with the tapered portion. Unlike a square needle, a round needle is not provided with a cutting edge at the tapered portion, so that the needle does not cut a tissue unnecessarily. Therefore, a tissue at the hole closely contacts the surface of a thread, which prevents body fluid and the like from being spilt from the sutured portion. With this characteristics, a round needle is mainly used for suturing blood vessels and soft tissues.

The above-mentioned round needle is manufactured in the following manner.

At first, a linear (straight shaped) material with a prescribed diameter is cut in a predetermined length. Then, a portion engaging a suture thread is formed at an end of the linear material. As the engaging portion, for instance, a spring eye, or a blind hole which is drilled in an axial direction of the linear material is adopted. Next, a tip and an intermediate portion of the material are ground with a whetstone or the like to form a sharp tip and a tapered portion. Then, rough buff polishing and another polishing with fine whetstone or the like are performed. Then, grinding stripes are removed through buff polishing, electrolytic polishing or the like to make mirror-finished surface. The straight material is bent to form a prescribed shape, and heat treatment and surface treatment are applied to complete the round needle.

In this connection, a demand for the sharpness of a needle, that is, the reduction of impalement resistance has been becoming considerably strong. However, it is difficult to increase the cutting quality of a round needle without cutting edge. In case of a square needle such as a triangular suture needle, as described above, edges at the pyramid-shaped tapered portion function as cutting edges to open a tissue while the needle proceeds in the tissue, so that it is relatively easy to reduce impalement resistance. However, in such a case, the square needle opens tissue with the edges thereof, therefor, cut section becomes large to cause poor sealing property after an impalement of the needle to decrease, resulting in spilt of body fluid. Therefore, the square needle is not suitable for the suture of blood vessels and the like.

To solve the above-mentioned problems, in prior art, the surface of the needle is mirror-finished to reduce the impalement resistance. That is, as a surface treatment in the above-mentioned manufacturing process, a finishing process through buff polishing, electrolytic polishing, chemical polishing or the like is carried out to form a mirror surface.

In the finishing process through buff polishing, cotton cloth, felt, or the like with fine abrasive grain is rotated and is pressed against the material to be ground to cause the abrasive grain to polish and finish the material, which allows a tip and a body of a needle to be mirror-finished.

In the finishing process through electrolytic polishing, electricity is forced to be applied to a needle to melt the surface of the needle through electrolysis.

In the finishing process through chemical grinding, unlike the finishing process through electrolytic grinding, electricity is not forced to be applied, but acid causes the surface of a needle to be melt. In this case also, polish and finished surface becomes mirror surface.

With the above-mentioned finishing processes, although the finished surface looks like a smooth mirror surface with naked eyes, it is not a mirror surface microscopically. For instance, with the buff finishing, many rough stripes caused by abrasive grain are observed.

Further, with respect to the electrolytic grinding, microscopically, it is confirmed that gases generated at the electrolysis adhere to the surface to form a rough surface with shallow craters.

With the chemical grinding, besides the rough surface with craters caused by the gases like the electrolytic polishing, further shallow roughness is formed on the surface of a needle by easily ground crystal grains and hardly ground crystal grains of the material of the needle.

As described above, there are all kinds of mirror-finishing, and whether a complete mirror surface or not is not automatically determined, in other words, the degree of the mirror finishing varies with material to be ground. For example, mirror-finishing for silicon wafer and that for plate member for constructing buildings are different from each other. In the detailed description of the invention, a mirror surface is defined to be such a finished surface of a needle as finished by generally used buff polishing, electrolytic polishing, or chemical polishing.

However, even with the more microscopically smooth mirror surface of a needle, the impalement resistance of the needle is not be reduced. In other words, there is no difference between the mirror surfaces formed through the buff polishing, electrolytic polishing, chemical polishing, and more smooth mirror surface.

In another method in the prior art for decreasing the impalement resistance, a tapered portion is coated with silicon. However, in this case, the silicon coating is peeled off after several impalements, thus, the effect of the silicon is significantly decreased.

To solve the above-mentioned problem, in Japanese Patent Publication No. Heisei 5-18576, it is proposed that channels with craters are formed on a tapered portion of a needle through chemical grinding, and silicon is applied onto the tapered portion. With such construction, silicon is sustained in the crater-like concave portions, and even after the needle is repeatedly used, the increase in the impalement resistance may be prevented.

However, in a suture needle in which silicon is sustained in the crater-like concave portions formed by the chemical polishing, as described above, the concave portions are very shallow as generally called as a mirror surface, the silicon is not so effective.

Further, in another Japanese Patent Publication No. Heisei 5-60746, it is disclosed that, in order to reduce the impalement resistance, a tapered portion near the tip of the needle is formed to be long to decrease the taper ratio (that is, the portion is formed to be thin and sharp).

However, when the taper ratio of the needle is decreased, such a needle is effective to a thin tissue but is not effective to a thick tissue as explained below.

Generally, it is known that there are two peaks of impalement resistance of a round needle. The first peak is observed when the tip of the needle enters a tissue, and the second peak is observed when the end of the tapered portion (the thickest portion) enters the tissue. In other words, the moment the tip of the needle just enters the tissue, the first peak is observed, and after that, the resistance is lowered once. Then, the resistance value gradually increases as the tapered portion becomes thicker, and when the end of the tapered portion, that is, when the thickest portion enters the tissue, the second peak is observed.

A sharper tip of a needle causes the first peak to be decreased. In other words, if a tissue is so thin that the tip of the tapered portion penetrates the tissue, the sharper tip is effective. However, when the tissue is thick in comparison to the long tapered portion, not only the long gentle tapered portion but also a short steep tapered portion contacts the tissue from the tip to the end of the needle, so that work loads of both tapered portions are the same (impalement resistance here is calculated by the following formula: impalement resistance=the coefficient of friction×pressure× distance that the tapered portion contacts the tissue).

As in the foregoing, the change in the taper ratio allows the pressure to be decreased, however, the distance that the tapered portion contacts the tissue becomes longer. Therefore, the sharper tip is not effective. This is applied not only to a round needle but to a needle with cutting edge only at the tip, so-called a cutting tapered needle. That is, the above problem is applicable to all types of needle without cutting edges at the tapered portion where the cross-section of the needle becomes large.

SUMMARY OF THE INVENTION

The present invention has been made in consideration of the above-mentioned fact and, it is therefore an object of the present invention to provide a suture needle in which impalement resistance is further decreased in comparison to a conventional one.

To achieve the above object, the suture needle according to the present invention comprising a base end portion, at an end of the suture needle, engaging a suture thread, a tip, at another end of the suture needle, impaling a tissue, and a tapered portion reaching to the tip, characterized in that the tapered portion is provided with a roughness of which stripe extends in a substantially axial direction thereof. This stripe roughness is solely provided on the tapered portion to improve the impalement resistance.

The stripe roughness is rougher and longer than the mirror surface of the suture needle described above. For example, the depth of the stripe roughness of the suture needle according to the present invention is approximately in the range between 2 $\mu$m and 15 $\mu$m while the surface roughness of the mirror surface of the suture needle is approximately in the range between 0.2 $\mu$m and 0.5 $\mu$m. This stripe roughness is formed by grinding with whetstone or the like, and rougher surface compared with this stripe roughness is excluded.

It is possible to mirror-finish only the tip portion of the tapered portion, or form cutting edge to the portion, or apply silicon treatment to the tapered portion.

Further, it is also possible that the tapered portion is not provided with a cutting edge; the stripe roughness is formed by grinding; the stripe roughness is more than twice as rough as that of a mirror surface; the stripe roughness is polished to a degree that the stripe disappears; a portion of the tapered portion near the tip of the suture needle has mirror surface; a portion of the tapered portion near the tip of the suture needle has a cutting edge; silicon treatment is applied to the tapered portion; length, in an axial direction of the suture needle, of the mirror surface at the portion of the tapered portion near the tip of the suture needle is 5% to 20% in length, in an axial direction, of the tapered portion; and length, in an axial direction of the suture needle, of the cutting edge at the portion of the tapered portion near the tip of the suture needle is 5% to 20% in length, in an axial direction, of the tapered portion.

BRIEF DESCRIPTION OF THE DRAWINGS

The present invention will be more apparent from the ensuring description with reference to the accompanying drawings, wherein.

DETAILED DESCRIPTION OF THE PREFERRED EMBODIMENTS

Hereafter, embodiments of the suture needle according to the present invention will be explained with reference to the drawings.

Figure 1:
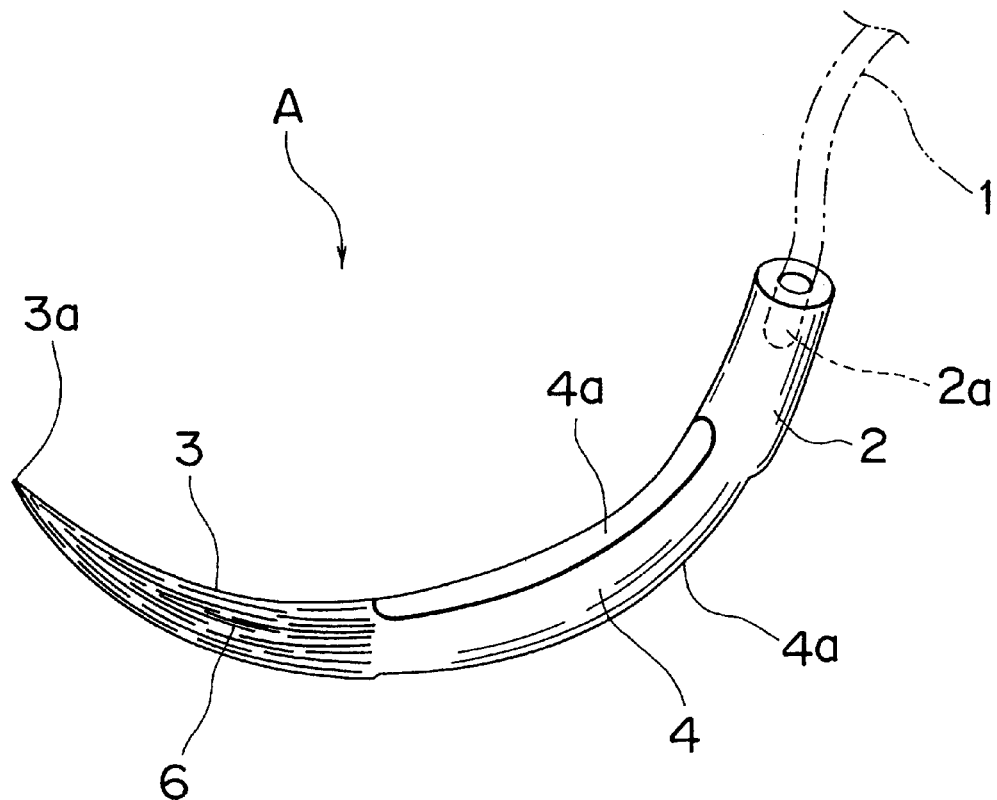
FIG. 1 is a perspective view showing an overall suture needle according to the present invention.

A suture needle A shown in FIG. 1 is a round needle, and a base end portion 2 engaging a suture thread 1 is provided at an end of the needle, and a blind hole 2a is drilled at the base end portion 2 in an axial direction of the needle, where the suture thread 1 is to be inserted and fixed.

At another end of the needle, a tapered portion 3, of which a diameter becomes larger as parting from a tip 3a is provided. The "tapered portion" used here is, as described above, defined to be a general shape of which a diameter or cross-section increases as parting from the tip of a needle. In this case, the change of the cross-section may be linear, as a matter of course, or curvilinear.

A portion between the base end portion 2 and tapered portion 3 is a body 4 of which diameter is substantially constant. In case of a round needle, the body 4 has a round cross-section, but ordinarily, two planes (planar surfaces) 4a, 4a which are in parallel with each other are formed through press working so that the needle is easily sustained by a needle-carrier at suturing work. Further, it is possible to provide four planes to form a square shape, which causes the needle to be more easily sustained and the strength of the needle to be increased.

Although the above is also applied to a conventional round needle, a round needle according to the present invention is characterized in that a stripe rough surface 6, of which stripes direct in a substantially, axial direction of the needle through grinding, is provided on the tapered portion 3. It should be noted that the strip rough surface 6 is provided only on the tapered portion 3.

Figure 2:
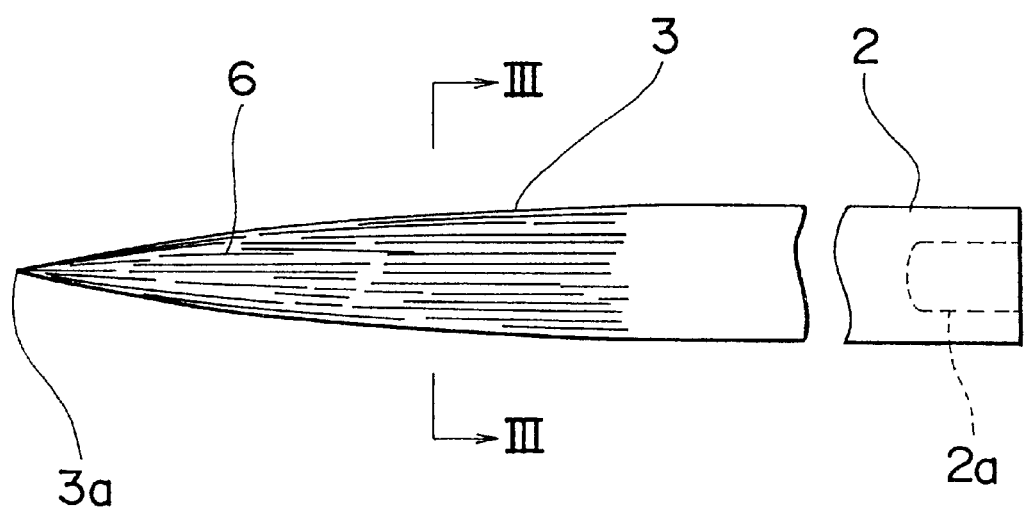
FIG. 2 is an enlarged view of the tapered portion and the base end portion, which are arranged in a row, of the suture needle shown in FIG. 1.
Figure 3:
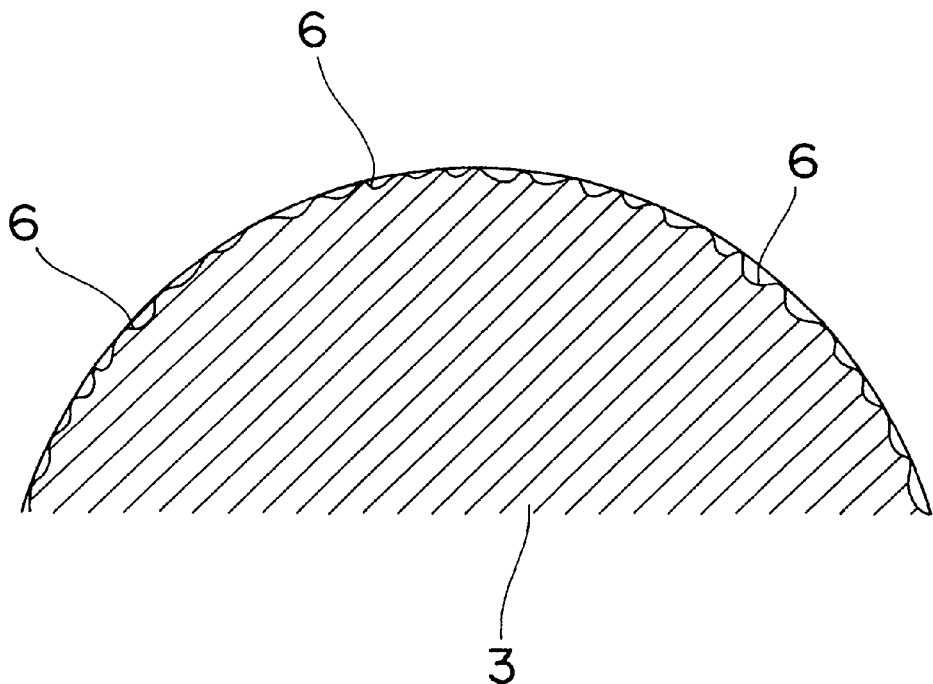
FIG. 3 is a cross-sectional view taken along the line III—III of FIG. 2, however, only an upper half thereof is illustrated.

FIG. 3 is an enlarged view of the tapered portion 3 of the suture needle shown in FIG. 2. As illustrated, the tapered portion 3 is provided with the stripe rough surface 6. This stripe rough surface is preferably formed by a whetstone regulated in ISO #30 to #320, a grinding belt, or the like. Further, the roughness of the stripe rough surface is preferably more than twice as rough as that of a mirror surface.

In the suture needle according to the above embodiment, when a tissue is pierced at a predetermined portion by the tip of the needle, a small clearance is formed between the stripe rough surface 6 and the tissue, so that the area where the stripe rough surface 6 and the tissue contact with each other decreases, allowing the tissue to be impaled by the suture needle with less force. Since the clearance is very small, and it is formed only when the tapered portion of the needle proceeds, which securely prevents body fluids from leaking after the proceeding of the needle, unlike the conventional one. Further, the size of the stripe roughness is larger than those formed by chemical polishing. With the crater-like roughness formed by chemical grinding, such fine clearances as described above are not generated, therefore, it is hardly expected to reduce the impalement resistance.

In this connection, the width or depth of the stripe roughness may freely be adjusted by selecting the number of abrasive grain for grinding and machining conditions. Further, when the stripe rough surface 6 is too rough or feel roughness after the grinding, it is preferable to slightly carry out a process of buff finishing, electrolytic polishing, chemical polishing, or the like after the grinding to smooth the stripe roughness.

Figure 4:
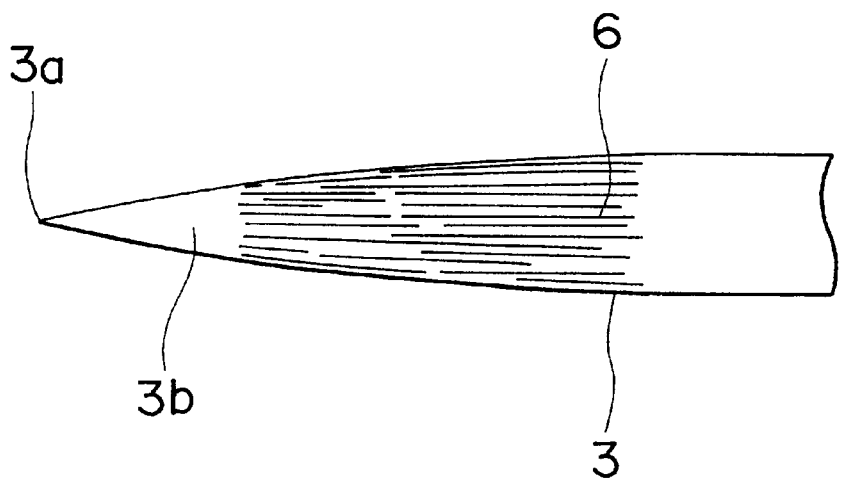
FIG. 4 shows the tip of the suture needle according to the second embodiment of the present invention.

FIG. 4 shows a suture needle according to the second embodiment of the present invention. In the above-mentioned embodiment, burrs formed at the machining with abrasive grain causes the tip of a needle not to be formed sharp. Then, only a tip portion 3b is formed to be mirror surface like the conventional one. Finishing method is selected from the buff finishing, electrolytic polishing, and chemical polishing. Further, the length l of the tip portion to be mirror finished is preferably about 5% to 20% of the length L of the tapered portion 3.

Figure 5A:
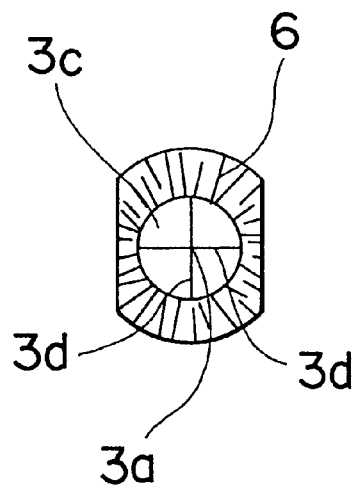
FIGS. 5a and FIG. 5b show the tip of the suture needle according to the third embodiment of the present invention.
Figure 5B:
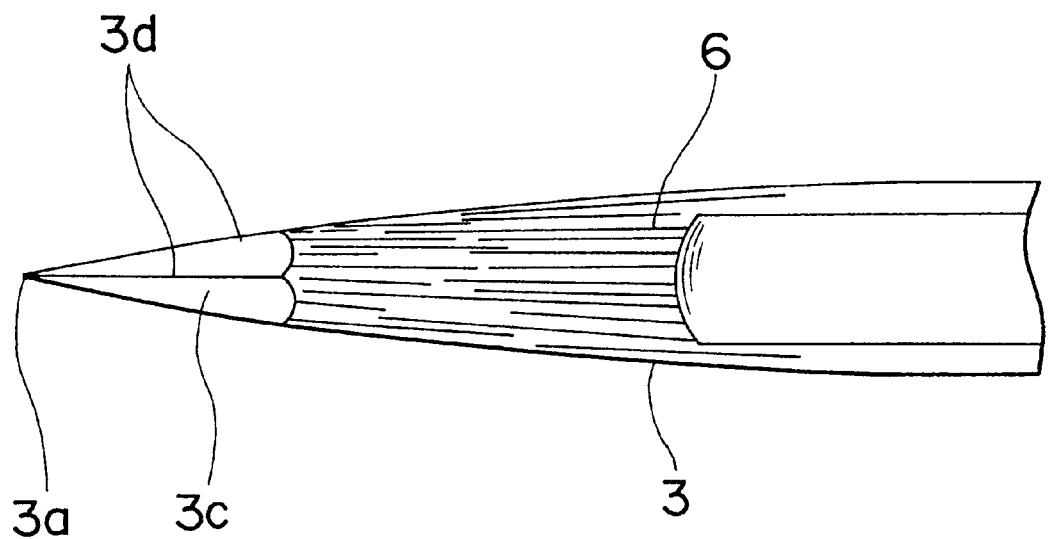

FIGS. 5(a) and 5(b) show a suture needle according to the third embodiment of the present invention. In this embodiment, only a tip portion 3c which is mirror finished as shown in FIG. 4 is formed to be a pyramid shape. Each edge 3d of the pyramid functions as a cutting edge to open a tissue and reduce the impalement resistance. However, this cutting edge is formed only on the tip portion 3c, and after the tip portion 3c enters the tissue, the stripe rough surface 6 impales the tissue. In this manner, the pyramid is formed only on a limited tip portion of the suture needle to eliminate a harmful influence that the tissue is cut too widely like the convention square needle, and moreover, the initial impalement resistance can be decreased.

In all the embodiments, conventionally used silicon treatment is preferably applied. With the silicon treatment, silicon enters the stripe roughness, so that the silicon is adequately maintained, which prevents the increase of the impalement resistance after repeated use of the suture needle.

Figure 6:
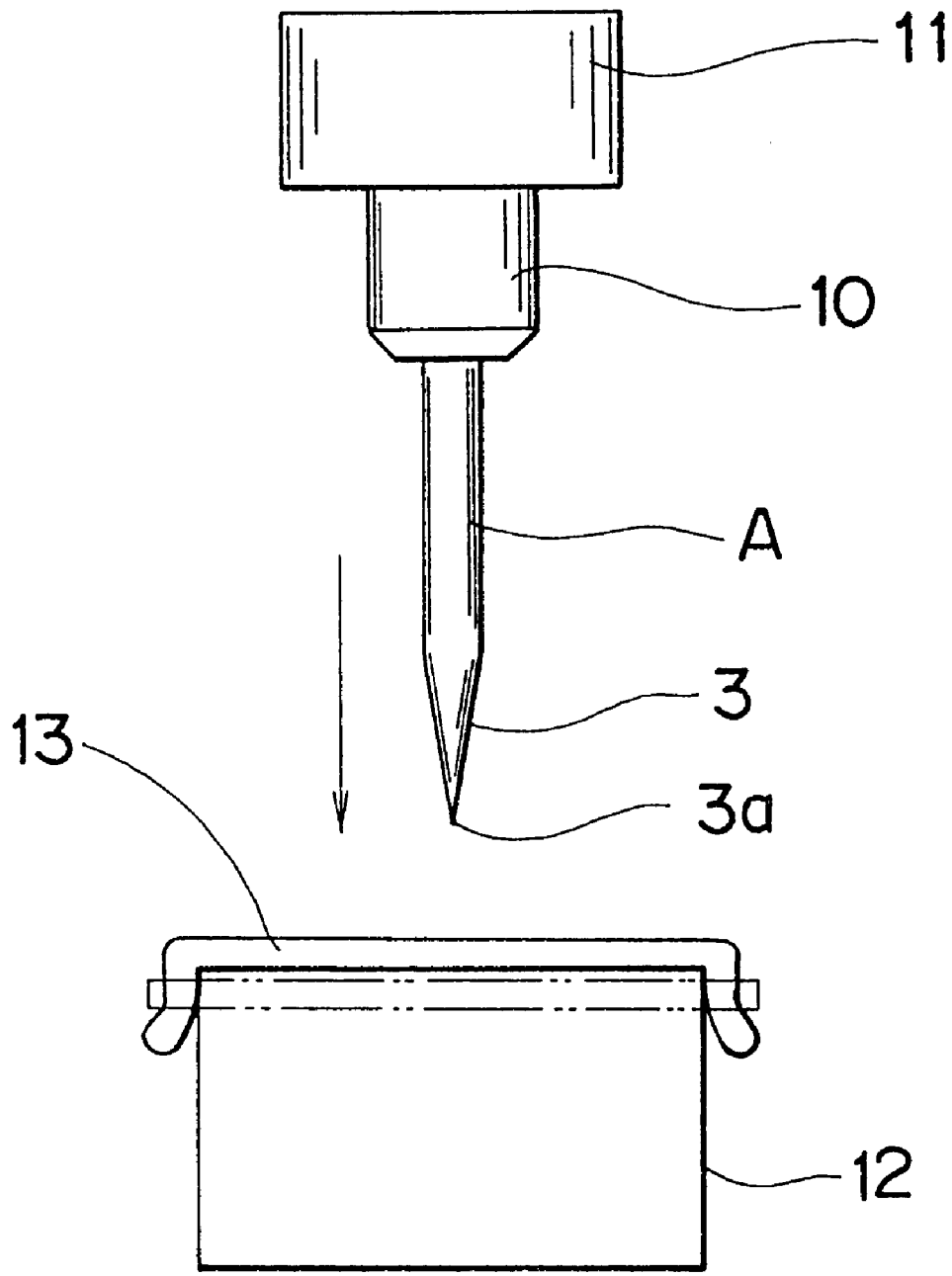
FIG. 6 is a diagram for explaining a method of measuring impalement resistance of a suture needle.

FIG. 6 is a drawing for explaining a method of measuring the impalement resistance of the suture needles according to the present invention. The suture needle A is maintained in a straight shape before bending, and is cramped by a vertically movable chuck 10. The chuck 10 is provided with a load cell 11. An upwardly opened box 12 is located below the suture needle A, and the opening of the upwardly opened box 12 is covered by an impalement material 13 (such as polyurethane with a thickness of 0.45 mm or a film-shaped "porvair" with a thickness of 1.10 mm made by Dow Corning Co.).

The chuck 10 is lowered by a driver (not shown), and the tip 3a of the suture needle A impales the impalement material 13. At this moment, the impalement resistance is measured by the load cell 11.

Figure 7:
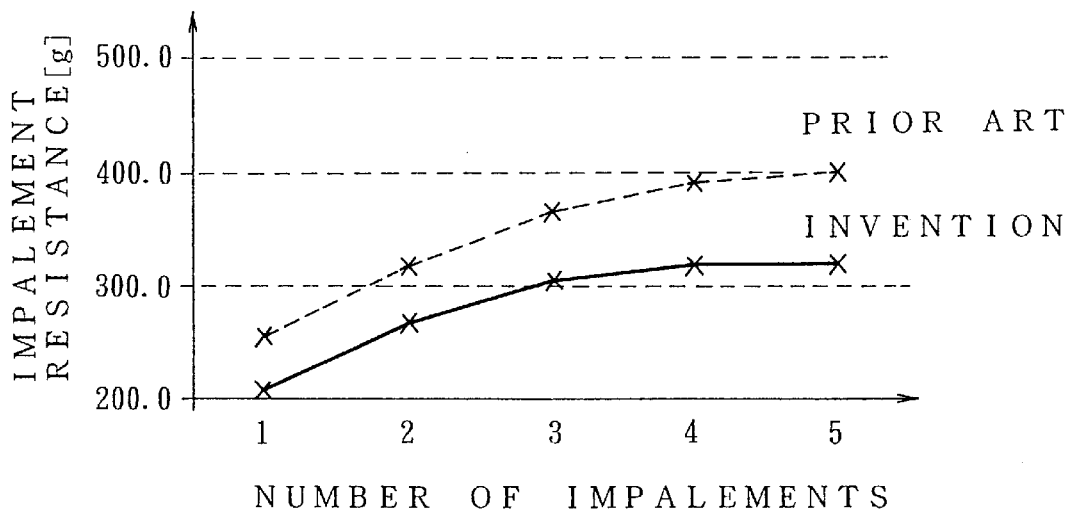
FIGS. 7 and 8 are graphs showing impalement resistance of the suture needles according to the present invention and conventional suture needles.
Figure 8:
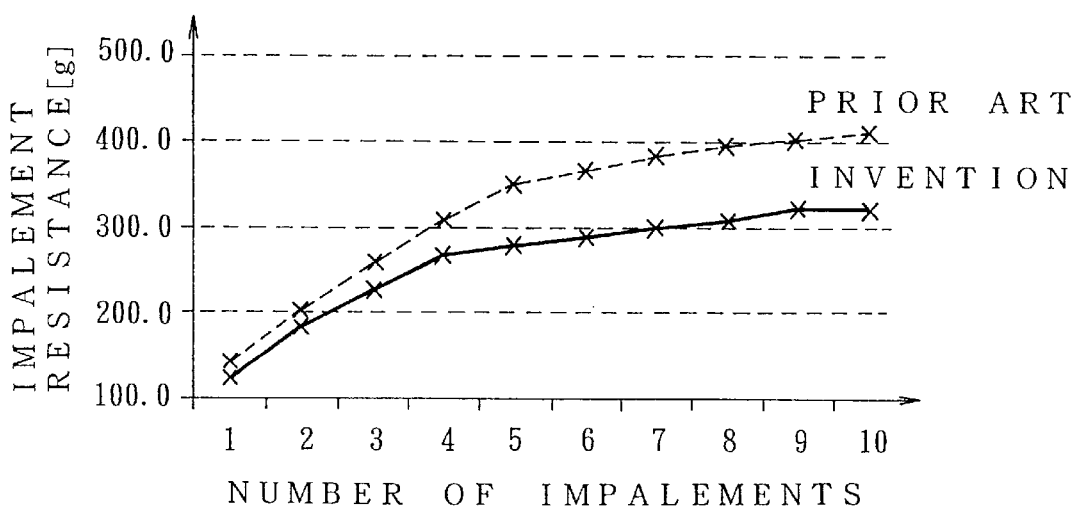

FIGS. 7 and 8 are graphs indicating the impalement resistance measured by the instrument illustrated in FIG. 6 when conventional suture needles and the suture needles according to the present invention are used. Solid lines show the impalement resistance when suture needles according to the present invention are used, and dotted lines show those of conventional suture needles. The suture needles according to the present invention have a stripe roughness (ground by the whetstone regulated in ISO #50) at a tapered portion, and a top is mirror-finished, and after that, chemical polishing is applied to the overall suture needle. The conventional suture needle is mirror-finished at an ordinary tapered portion thereof through buff machining, and after that, chemical polishing is applied to the overall suture needle.

The suture needles shown in FIG. 7 are not subject to silicon treatment, but the suture needles in FIG. 8 are treated by silicon ("MDX-4159" made by Dow Corning Co.) after the same process to the suture needles of FIG. 7. The depth (surface roughness) of the stripe of the suture needle according to the present invention is approximately in the range of 2 $\mu$m–15 $\mu$m. In contrast, the surface roughness of the mirror surface of the suture needle is approximately in the range of 0.2 $\mu$m–0.5 $\mu$m.

The suture needles without silicon treatment impaled the impalement material 13 five times, and the impalement resistance at each impalement was measured with the load cell. The suture needles with the silicon coating impaled ten times, and the impalement resistance at each impalement was measured.

In the both cases of FIGS. 7 and 8, it is clearly recognized that the suture needles according to the present invention are superior to the conventional suture needles. Especially, as shown in FIG. 8, there is not much difference between the both suture needles with the silicon coating until four impalements. However, after that, the difference between the present invention and conventional technology becomes larger as the number of impalements increases. This is because the repeated impalements causes the silicon applied to the conventional suture needle to gradually be peeled off, while, in the present invention, the silicon is sustained on the stripe roughness and the effect of the silicon treatment continues.

Although the above explanation is made for a round suture needle, it is possible to form the stripe roughness through grinding according to the present invention to tapered portions of a square needle and a dull needle and the same effects of the invention can be obtained. Further, the same effects can be obtained even if the engaging portion with a suture thread is a blind hole or a spring eye; the shape of cross-section of a body was oval or a cross-section which is sandwiched between two substantially parallel planes and a central portion is constricted; and the needle is bent or straight. However, the advantage of the present invention is most effectively achieved when the suture needle is not provided with cutting edge at a tapered portion thereof.

As described above, with the present invention, a suture needle comprising a base end portion, at an end of the suture needle, engaging a suture thread, a tip, at another end, impaling a tissue, a tapered portion reaching to the tip, is characterized in that the tapered portion is provided with stripe roughness through grinding, so that small clearances are formed between the stripe roughness and the tissue, resulting in decrease of the impalement resistance.

Although only a preferred embodiment is specifically illustrated and described herein, it will be appreciated that many modifications and variations of the present invention are possible in light of the above teachings and within the purview of the appended claims without departing the spirit and intended scope of the invention.

What is claimed is:

1. A suture needle, comprising:
    a base end portion, at an end of said suture needle, for engaging a suture thread;
    a tip portion, at another end of said suture needle, for impaling a tissue; and
    a tapered portion reaching to said tip portion, said tapered portion having a cross-section without a cutting edge and a plurality of roughened regions formed in stripes extending in a substantially axial direction of said tapered portion, said roughened regions being provided solely on said tapered portion and having a surface roughness of about 2 $\mu$m–15 $\mu$m.

2. The suture needle as claimed in claim 1, wherein said roughened regions are polished to increase their smoothness.

3. The suture needle as claimed in claim 1, wherein a portion of said tapered portion near the tip has a polished surface.

4. The suture needle as claimed in claim 1, wherein the tip portion has a cutting edge.

5. The suture needle as claimed in claim 1, wherein a silicon coating is applied to said tapered portion.

6. The suture needle as claimed in claim 3, wherein length, in an axial direction of the suture needle, of said polished surface at said portion of said tapered portion near the tip is 5% to 20% in length, in an axial direction, of said tapered portion and a surface roughness of said polished surface is about 0.2 $\mu$m–0.5 $\mu$m.

7. The suture needle as claimed in claim 4, wherein length, in an axial direction of the suture needle, of said cutting edge at said tip portion is 5% to 20% in length, in an axial direction, of said tapered portion and a surface roughness of said cutting edge is about 0.2 $\mu$m–0.5 $\mu$m.

* * * * *